United States Patent
Horiuchi et al.

(10) Patent No.: US 7,643,766 B2
(45) Date of Patent: Jan. 5, 2010

(54) DEVICE FOR MEASURING CONCENTRATION OF TONER IN LIQUID DEVELOPER, IMAGE FORMING APPARATUS PROVIDED THEREWITH, AND METHOD FOR MEASURING TONER CONCENTRATION

(75) Inventors: Nobuhiro Horiuchi, Osaka (JP); Koji Murase, Osaka (JP); Hiroyuki Ueda, Osaka (JP); Hidenori Takenaka, Osaka (JP); Tomoyuki Oda, Osaka (JP); Jumpei Hobo, Osaka (JP)

(73) Assignee: Kyocera Mita Corporation, Osaka (JP)

( * ) Notice: Subject to any disclaimer, the term of this patent is extended or adjusted under 35 U.S.C. 154(b) by 182 days.

(21) Appl. No.: 11/907,612

(22) Filed: Oct. 15, 2007

(65) Prior Publication Data

US 2009/0003852 A1  Jan. 1, 2009

(30) Foreign Application Priority Data

Oct. 19, 2006 (JP) .............................. 2006-284710
Jul. 20, 2007 (JP) .............................. 2007-189417

(51) Int. Cl.
*G03G 15/10* (2006.01)
*G01N 21/59* (2006.01)

(52) U.S. Cl. .............................. 399/57; 340/619; 399/64

(58) Field of Classification Search .................. 399/57, 399/58, 62, 64, 30; 340/618, 619; 73/53.01; 324/71.1

See application file for complete search history.

(56) References Cited

U.S. PATENT DOCUMENTS

| | | | | |
|---|---|---|---|---|
| 4,660,152 A | * | 4/1987 | Downing et al. | 399/62 X |
| 5,319,421 A | * | 6/1994 | West | 399/59 |
| 5,899,605 A | * | 5/1999 | Caruthers et al. | 399/57 X |
| 5,960,231 A | * | 9/1999 | Martinez | 399/30 |
| 6,377,760 B1 | * | 4/2002 | Hagiwara | 399/30 |

FOREIGN PATENT DOCUMENTS

| | | | |
|---|---|---|---|
| JP | 07-063678 A | * | 3/1995 |
| JP | 2004-093570 A | * | 3/2004 |
| JP | 2005-315948 | | 11/2005 |

OTHER PUBLICATIONS

Machine translation of JP 2005-315948 A dated Jun. 11, 2009.*

* cited by examiner

*Primary Examiner*—Sophia S Chen
(74) *Attorney, Agent, or Firm*—Smith, Gambrell & Russell, LLP

(57) ABSTRACT

Provided are a light-emitting portion having a light-emitting member and a light emergence surface through which light from the light-emitting member emerges, and a light-receiving portion having a light incidence surface through which the light from the light-emitting member enters and a light-receiving member that detects the light entering through the light incidence surface. The light-emitting portion and the light-receiving portion can make relative movement between a measurement position in which the light emergence surface and the light incidence surface make contact with each other and a waiting position in which the light emergence surface is away from the light incidence surface. When the light-emitting portion and the light-receiving portion are in the measurement position, the light emergence surface and the light incidence surface make contact with each other at a point.

18 Claims, 12 Drawing Sheets

-- Prior Art --

-- Prior Art --

-- Prior Art --

DEVICE FOR MEASURING CONCENTRATION OF TONER IN LIQUID DEVELOPER, IMAGE FORMING APPARATUS PROVIDED THEREWITH, AND METHOD FOR MEASURING TONER CONCENTRATION

This application is based on Japanese Patent Applications Nos. 2006-284710 and 2007-189417 filed on Oct. 19, 2006 and Jul. 20, 2007 respectively, the contents of which are hereby incorporated by reference.

BACKGROUND OF THE INVENTION

1. Field of the Invention

The present invention relates to devices for measuring the concentration of toner in a liquid developer by detecting the amount of light passing through the liquid developer, to image forming apparatuses provided with such devices, and to toner concentration measuring methods.

2. Description of Related Art

Developing methods used in image forming apparatuses are broadly classified into dry developing and wet developing. Previously, dry developing was widely used from the viewpoint of ease of handling and reduction in size and weight. In recent years, however, wet developing has been receiving new attention from the viewpoint of, for example, improving the quality of images.

In wet developing, a liquid developer made of a carrier liquid, such as silicone or paraffin, and toner particles suspended in the carrier liquid is used to develop an electrostatic latent image formed on the surface of a photoconductor based on image data. To obtain an image of high quality by wet developing, it is important to keep the toner concentration in the liquid developer at an appropriate level.

Therefore, in JP-A-2005-315948, a recess is formed in the inner wall surface of a liquid developer reservoir, and a phototransmitter is provided in the bottom of the recess. In addition, a movable body is provided in such a way that it can move close to or away from the inner wall surface, and a photoreceptor is provided in the movable body in a face thereof facing the phototransmitter. When toner concentration is measured, the movable body is moved so as to make close contact with the inner wall surface, such that a liquid developer is trapped in the narrow space between the movable body and the inner wall surface. The liquid developer trapped therein is irradiated with light emitted from the phototransmitter, and the amount of light passing through the liquid developer and reaching the photoreceptor is detected. In this way, the toner concentration is measured.

In this case, when the toner concentration of a liquid developer using toner having a low light transmission, such as black, is measured, a thick layer of liquid developer prevents measurement light from passing therethrough. This makes high-accuracy measurement impossible. To avoid this problem, it is necessary to trap the liquid developer as thin as on the order of several tens of μm. However, due to the difficulty in forming a recess having a depth of several tens of μm, a spacer is used instead for forming a narrow space in which a liquid developer is trapped. FIGS. 12A and 12B each show a toner concentration measuring device in which a narrow space is formed by using spacers. The toner concentration measuring device shown in FIGS. 12A and 12B has a light-emitting portion 101 and a light-receiving portion 102. The light-receiving portion 102 is provided with a light incidence surface 122a and a light-receiving member 105 that is so disposed as to face the light-emitting portion 101 with the light incidence surface 122a between them. The light-receiving portion 102 is attached to the measuring tank 103 in such a way that the light incidence surface 122a is flush with the bottom of the measuring tank 103. On the other hand, the light-emitting portion 101 has a light-emitting member 104 and a light emergence surface 112a from which light emitted from the light-emitting member 104 emerges, and the light-emitting portion 101 is attached in such a way as to permit the light emergence surface 112a to move up and down with respect to the light incidence surface 122a. At the bottom of the measuring tank 103 near the light incidence surface 122a are provided spacers 107a and 107b, each being formed of a metal plate that is several tens of μm thick, in such a way that they face each other with the light incidence surface 122a disposed between them.

As shown in FIG. 12B, when toner concentration is measured, the light-emitting portion 101 is moved downward until the bottom surface of the light-emitting portion 101 makes contact with the top faces of the spacers 107a and 107b. This creates a space having a predetermined thickness (equal to the thickness of the spacers 107a and 107b) between the light emergence surface 112a and the light incidence surface 122a. The liquid developer (not shown) trapped in this space is irradiated with light emitted from the light-emitting portion 101, and the amount of light passing through the liquid developer and reaching the light-receiving member 105 through the light incidence surface 122a is detected by the light-receiving member 105. In this way, the toner concentration is measured.

Disadvantageously, by the former method in which the space is formed by the formation of a recess, the toner may accumulate in the recess formed in the inner wall surface, making it impossible to measure the toner concentration with high accuracy. By the latter method in which the space is formed by using spacers, as shown in FIG. 13, toner T may be stuck between the bottom of the measuring tank 103 and the spacers 107a and 107b, making the space wider than a predetermined value. To avoid this problem, the spacers 107a and 107b may be bonded to the bottom of the measuring tank 103 with an adhesive or the like. However, it is technically difficult to control the thickness of a coating of adhesive in micrometers.

SUMMARY OF THE INVENTION

In view of the conventionally experienced problems described above, it is an object of the present invention to provide toner concentration measuring devices that, despite having a simple structure, can measure the toner concentration of a liquid developer with high accuracy and stability, and to provide image forming apparatuses provided with such toner concentration measuring devices.

According to one aspect of the present invention, a toner concentration measuring device for a liquid developer is provided with: a light-emitting portion having a light-emitting member and a light emergence surface from which light from the light-emitting member emerges; and a light-receiving portion having a light incidence surface through which the light from the light-emitting member enters and a light-receiving member that detects the light entering through the light incidence surface. The light emergence surface and the light incidence surface can make relative movement between a measurement position in which the light emergence surface and the light incidence surface make contact with each other and a waiting position in which the light emergence surface and the light incidence surface are away from each other. The light emergence surface and the light incidence surface make contact with each other at a contact point or along a contact line in the measurement position.

In the toner concentration measuring device according to the present invention, at least one of the light emergence surface and the light incidence surface is a spherical surface protruding outward or has a protruding portion protruding outward, and the light emergence surface and the light incidence surface make contact with each other at a point or along a line in the measurement position. Thus, unlike the conventional example, the toner is prevented from accumulating in a recess or from being stuck between the bottom of the measuring tank and the spacer. This makes it possible to measure the toner concentration with high accuracy and stability.

Here, from the viewpoint of achieving measurement with high accuracy and stability, it is preferable that one of the light emergence surface and the light incidence surface be spherical in shape, and the other be planar in shape.

When one of the light emergence surface and the light incidence surface is spherical in shape and the other is planar in shape, it is possible to achieve measurement with higher accuracy and stability.

Preferably, the direction in which the light-emitting member emits light and the direction in which the light enters the light-receiving member are on approximately the same axis, and the axis is made to pass through a predetermined region including a point at which or a line along which the light emergence surface and the light incidence surface make contact with each other. Alternatively, the axis is made to pass outside of a predetermined region including a point at which or a line along which the light emergence surface and the light incidence surface make contact with each other. When the axis is made to pass through a predetermined region including a point at which or a line along which the light emergence surface and the light incidence surface make contact with each other, it is preferable that a lightproof member be attached to a predetermined region around the contact point or the contact line, the predetermined region of at least one of the light emergence surface and the light incidence surface, to achieve measurement with higher accuracy. More preferably, the lightproof member is formed with a first lightproof member covering the contact point or the contact line and a second lightproof member that is attached around the first lightproof member leaving a space between the first lightproof member and the second lightproof member.

From the viewpoint of achieving measurement with higher accuracy, it is preferable that the direction in which the light-emitting member emits light and the direction in which the light enters the light-receiving member be on approximately the same axis, and the light-emitting member and the light-receiving member be at a fixed distance from each other regardless of whether in the waiting position or in the measurement position.

The present invention is directed also to an image forming apparatus incorporating the toner concentration measuring device described above.

By incorporating the toner concentration measuring device of the present invention into an image forming apparatus provided with a wet developing device, it is possible to measure the toner concentration of a liquid developer with high accuracy and stability. This makes it easy to control the toner concentration. Thus, it is possible to offer an image forming apparatus that can effectively prevent degradation in image quality, such as nonuniformity of color or variations in density due to variations in concentration of the liquid developer.

The present invention is directed also to a toner concentration measuring method using the toner concentration measuring device described above.

With the toner concentration measuring method using the toner concentration measuring device described above, unlike the conventional example, the toner is prevented from accumulating in a space between the light emergence surface and the light incidence surface. This makes it possible to measure the toner concentration of the liquid developer flowing through the measuring tank with high accuracy.

From the viewpoint of ensuring that local accumulation of toner is prevented, it is preferable that the light emergence surface or the light incidence surface be moved from the measurement position to the waiting position in such a way that, when the shortest distance between the light emergence surface and the light incidence surface becomes about half the thickness of the liquid developer flowing through the measuring tank, a movement of the light-emitting portion or the light-receiving portion is temporarily stopped, the light-emitting portion or the light-receiving portion is left in this position for a specified time, and then the light emergence surface or the light incidence surface is finally moved to the waiting position.

DETAILED DESCRIPTION OF PREFERRED EMBODIMENTS

Figure 1:
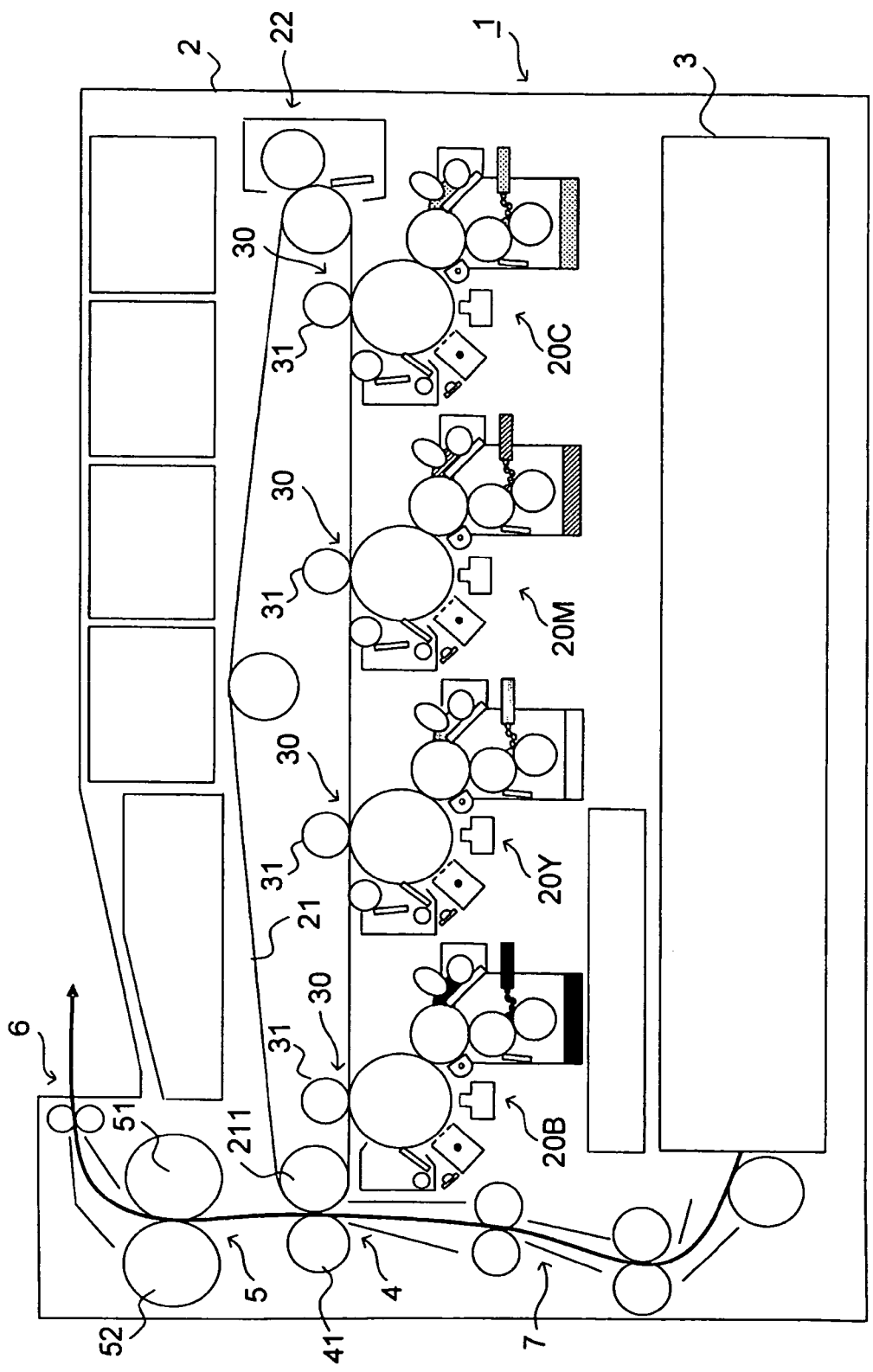
FIG. 1 is a front sectional view showing an image forming apparatus incorporating a toner concentration measuring device according to the invention.

Hereinafter, an embodiment of the present invention will be described with reference to the accompanying drawings. First, an outline of the structure and image forming operation of an image forming apparatus incorporating a toner concentration measuring device according to the invention will be described with reference to FIG. 1. FIG. 1 is a front sectional view showing an essential portion of the image forming apparatus. This image forming apparatus is a tandem-type color printer that transfers a toner image to paper by using an intermediate transfer belt.

As shown in FIG. 1, a color printer 1 is primarily built with a paper accommodating portion 3 that accommodates sheets of paper, a secondary transfer portion 4 that transfers a toner image formed by an image forming portion 2 to paper, a fixing portion 5 that fixes the transferred toner image to the paper, a paper ejecting portion 6 that ejects the paper to which the image is fixed, a paper conveyer portion 7 that conveys the paper from the paper accommodating portion 3 to the paper ejecting portion 6, a liquid developer circulating device 8 (see FIG. 3), and image forming portions 20C, 20M, 20Y, and 20B.

The paper accommodating portion 3 is removably mounted inside a lower portion of the body of the apparatus. The paper accommodating portion 3 accommodates sheets of paper (not shown) such as yet-to-be-printed sheets of paper. The paper fed from the paper accommodating portion 3 is conveyed vertically upwards by the paper conveyer portion 7 along the left-hand inner surface of the apparatus body 2 to the secondary transfer portion 4. The secondary transfer portion 4 transfers a toner image formed on an intermediate transfer belt 21 to the paper, and is built with a supporting roller 211 that supports the intermediate transfer belt 21 and a secondary transfer roller 41 that is disposed so as to face the supporting roller 211.

The fixing portion 5 fixes the toner image to the paper, and is disposed above the secondary transfer portion 4. The fixing portion 5 includes a heating roller 51 that makes contact with the toner image transferred to the paper, and a pressure roller 52 that is disposed so as to face the heating roller 51. The paper ejecting portion 6 ejects the paper to which the toner image is fixed by the fixing portion 5, and is disposed in the upper part of the color printer 1.

Above the paper accommodating portion 3 are disposed the image forming portion 20C for cyan, the image forming portion 20M for magenta, the image forming portion 20Y for yellow, and the image forming portion 20B for black. Above the image forming portions 20C, 20M, 20Y, and 20B is provided the intermediate transfer belt 21. The image forming portions 20C, 20M, 20Y, and 20B are arranged between a belt cleaning device 22 and the secondary transfer portion 4 which are located most upstream and most downstream, respectively, along a rotation direction of the intermediate transfer belt 21, so as to be disposed in parallel and in contact with the intermediate transfer belt 21. The image forming portions 20C, 20M, 20Y, and 20B may be arranged in any other way than is specifically described above. However, with consideration given to the influence of color mixture on the final image, the arrangement described above is preferable. The structure of the image forming portions 20C, 20M, 20Y, and 20B will be described later.

The intermediate transfer belt 21 serving as an intermediate transfer body is supported in such a way that it is stretched around a plurality of rollers, and is rotated clockwise in FIG. 1 by an unillustrated driving device. Used as the intermediate transfer belt 21 is a dielectric resin sheet that is formed into an endless belt by bonding the two ends of the sheet together or into a seamless belt. Hereinafter, one side of the intermediate transfer belt 21, facing outward, is referred to as a front side, and the other side thereof is referred to as a back side.

Above each of the image forming portions 20C, 20M, 20Y, and 20B is provided a primary transfer roller 31 with the intermediate transfer belt 21 interposed therebetween. The primary transfer roller 31 can be moved up and down in FIG. 1. If necessary, the primary transfer rollers 31 are each pressed against a corresponding one of photoconductor drums 10 (see FIG. 2) of the image forming portions 20C, 20M, 20Y, and 20B with the intermediate transfer belt 21 interposed therebetween, thereby forming primary transfer portions 30. In these primary transfer portions 30, toner images formed by the image forming portions 20C, 20M, 20Y, and 20B are transferred to the surface of the intermediate transfer belt 21. As a result of the toner images formed by the image forming portions 20C, 20M, 20Y, and 20B being sequentially transferred to the intermediate transfer belt 21 with predetermined timing as the intermediate transfer belt 21 is driven and rotated, the toner images of four colors, namely, cyan, magenta, yellow, and black, are superimposed on one another, whereby a full-color image is formed on the surface of the intermediate transfer belt 21.

The full-color image formed on the surface of the intermediate transfer belt 21 is transferred to the paper conveyed by the paper conveyer portion 7 in synchronism with the timing with which an image is formed. This transfer is performed in the secondary transfer portion 4 built with the intermediate transfer belt 21 and the secondary transfer roller 41 which are pressed against each other.

After the secondary transfer, the developer remaining on the surface of the intermediate transfer belt 21 is removed therefrom by the belt cleaning device 22 located upstream of the image forming portion 20C for cyan along a rotation direction of the intermediate transfer belt 21, and is collected by a waste toner container (not shown).

Figure 2:
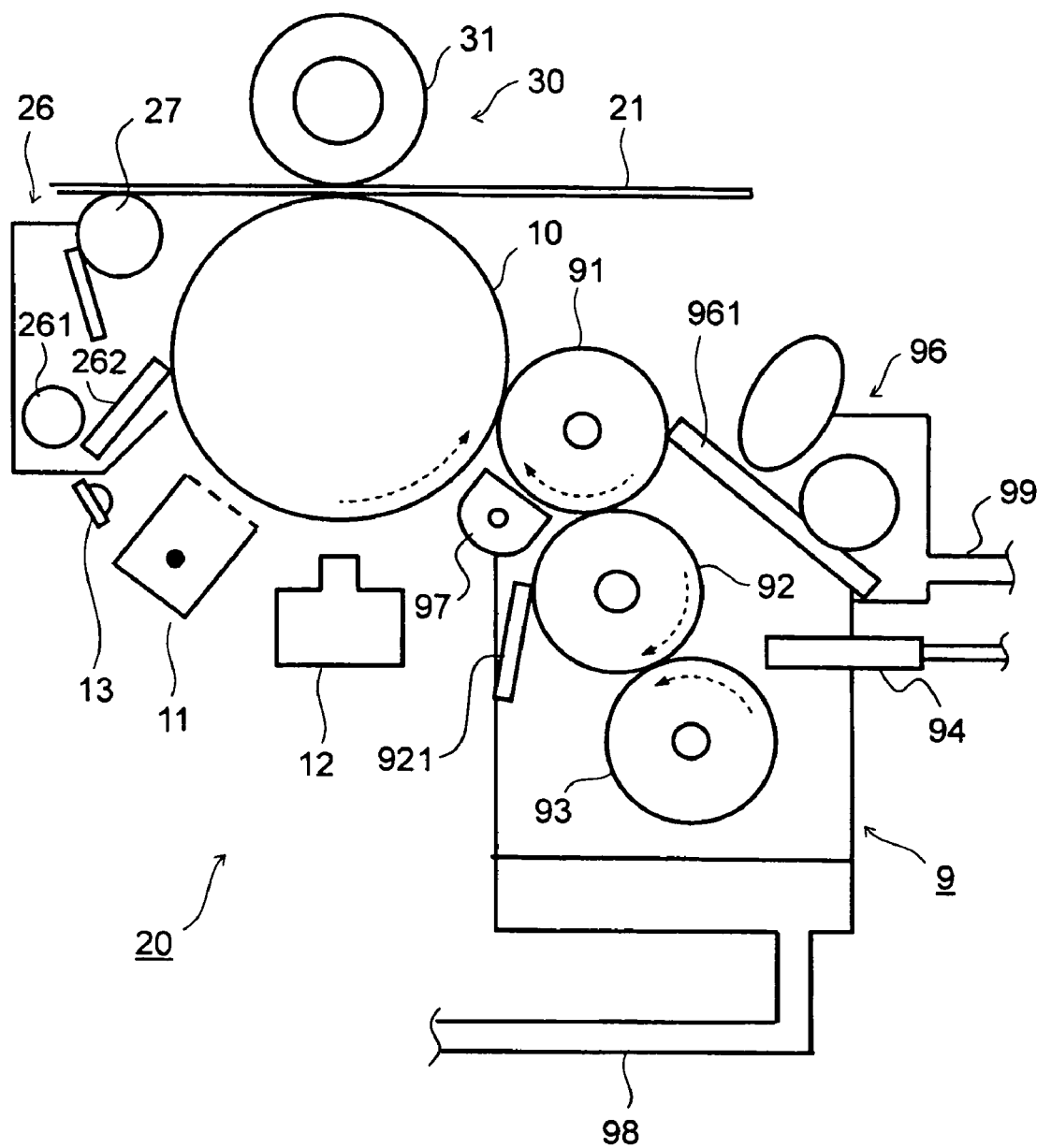
FIG. 2 is an enlarged view of a part of the image forming apparatus shown in FIG. 1 around the image forming portion.

FIG. 2 is an enlarged view f a part of the image forming apparatus shown in FIG. 1 around the image forming portion. With reference to FIG. 2, the detailed structure of the image forming apparatus 1 around the image forming portions 20C, 20M, 20Y, and 20B will be described. Since the image forming portions 20C, 20M, 20Y, and 20B for four different colors have a common structure, the identification characters, namely, "C", "M", "Y", and "B" as in the image forming portions 20C, 20M, 20Y, and 20B, will be omitted. It should be noted that, among the image forming portions, only the image forming portion 20B which is closest to the secondary transfer portion 4 does not have a carrier liquid removing roller 27 used for improving the primary transfer characteristics of an image forming portion located downstream thereof. The reason is that the image forming portion 20B does not need to remove a carrier liquid because no image forming portion is located downstream thereof. Incidentally, dashed arrows in FIG. 2 indicate different directions in which the different rotating members rotate.

The image forming portions 20 each include a photoconductor drum 10 serving as an electrostatic latent image supporting member, a charger 11 serving as a charging device, an LED exposing device 12 serving as an exposing device, a developing device 9, a primary transfer roller 31 serving as a transferring device, a cleaning device 26, a discharger 13, and a carrier liquid removing roller 27. Each image forming portion 20 forms a toner image by using a liquid developer made of an insulating liquid (a carrier liquid) and toner particles suspended therein. The liquid developer is fed from the liquid developer circulating device 8 (see FIG. 3) to the developing device 9. Based on the image data, such as characters, graphics, and patterns, received from an external computer (not shown), an electrostatic latent image is formed on the photoconductor drum 10. The electrostatic latent image thus formed is then developed into a visible image (a toner image) by the developing device 9.

The photoconductor drum 10 is a cylindrical member built with a conductive substrate formed of aluminum or the like and an amorphous silicon layer, which is an inorganic photoconductive material, formed on the outer circumferential surface of the conductive substrate by glow discharge deposition, for example. The photoconductor drum 10 can support, on the surface thereof, a toner image including charged toner (in this embodiment, positively charged toner). In this embodiment, an amorphous silicon photoconductor that is charged positively is used. Since reversal development is adopted, used as the toner forming a liquid developer is toner that can be charged positively. The photoconductor drum 10 is made to rotate counterclockwise in the figure by an unillustrated driving device, so that the circumferential velocity thereof becomes substantially equal to the velocity at which paper is conveyed (e.g., 210 mm/s).

The charger 11 uniformly charges the surface of the photoconductor drum 10. Used as the charger 11 is a corona discharge device that discharges when a high voltage is applied to a thin wire or the like used as an electrode thereof.

The LED exposing device 12 is disposed downstream of the charger 11 along a rotation direction of the photoconductor drum 10. The LED exposing device 12 has an LED light source. The LED exposing device 12 illuminates the charged surface of the photoconductor drum 10 with light commensurate with the image data, such that the potential of the illuminated area is optically attenuated. In this way, an electrostatic latent image is formed on the surface of the photoconductor drum 10. Alternatively, an LSU (laser scanning unit) or the like may be used instead of the LED exposing device 12.

As mentioned earlier, the developing device 9 develops the electrostatic latent image formed on the surface of the photoconductor drum 10 into a toner image by using a liquid developer made of an insulating liquid and toner particles suspended therein. The detailed structure of the developing device 9 will be described later.

The primary transfer roller 31 serving as a transfer device is so disposed as to make contact with the back side of a portion of the intermediate transfer belt 21, the portion where the intermediate transfer belt 21, on the front side thereof, makes contact with the photoconductor drum 10. To the primary transfer roller 31, a voltage (in this embodiment, a negative voltage) that is opposite in polarity to the charge of the toner of the toner image formed on the surface of the photoconductor drum 10 is applied from an unillustrated electric power source. That is, the primary transfer roller 31 applies, to the intermediate transfer belt 21, a voltage that is opposite in polarity to the charge of the toner in a position where the primary transfer roller 31 makes contact with the intermediate transfer belt 21. Since the intermediate transfer belt 21 has conductivity, the applied voltage causes the toner to be attracted to the front side of the intermediate transfer belt 21 and a part around it.

The cleaning device 26 removes the developer remaining on the surface of the photoconductor drum 10 without being transferred from the photoconductor drum 10 to the intermediate transfer belt 21. The cleaning device 26 is provided with a residual developer conveying screw 261 and a drum cleaning blade 262. The residual developer conveying screw 261 conveys, to the outside of the cleaning device 26, the liquid developer removed from the photoconductor drum 10 by the drum cleaning blade 262, and the carrier liquid removed from the intermediate transfer belt 21 by the carrier liquid removing roller 27, which will be described later. The residual developer conveying screw 261 is provided inside the cleaning device 26. The drum cleaning blade 262 is brought into contact with the surface of the photoconductor drum 10 in such a way as to rub against it. The drum cleaning blade 262 scrapes the residual developer off the surface of the photoconductor drum 10, and is provided in the form of a plate extending in the direction along the longer sides of the photoconductor drum 10 (in the direction perpendicular to the plane of FIG. 2). The liquid developer removed from the surface of the photoconductor drum 10 by the cleaning device 26 is moved toward the residual developer conveying screw 261 by gravity, is then conveyed to the outside of the cleaning device 26 by the residual developer conveying screw 261, and is then collected by a first recovery container 81 (see FIG. 3).

The discharger 13 has a light source such as an LED (light-emitting diode). After the developer is removed by the drum cleaning blade 262, the discharger 13 removes charge remaining on the surface of the photoconductor drum 10 by emitting light from the light source, thereby making the photoconductor drum 10 ready for the next image formation. The carrier liquid removing roller 27 removes the carrier liquid from the surface of the intermediate transfer belt 21. The carrier liquid removing roller 27 is a nearly cylindrical member that can rotate around a rotation axis parallel to the rotation axis of the photoconductor drum 10 in the same direction as the photoconductor drum 10. The carrier liquid removing roller 27 is disposed downstream of a position where the photoconductor drum 10 and the intermediate transfer belt 21 make contact with each other along the direction in which the belt moves.

Next, the structure and developing operation of the developing device 9 will be described in detail with reference to FIG. 2. Here, a liquid developer used in the developing device 9 is made of a carrier liquid that is a nonpolar insulating liquid such as silicone oil or the like, and toner particles in the form of fine resins that becomes positively charged, the toner particles being suspended in the carrier liquid.

The developing device 9 is provided for feeding the liquid developer to the photoconductor drum 10, and is provided with a developing roller 91, a feeding roller 92, a supporting roller 93, a developer feeding member 94, a developer remover 96, and a developer charger 97. The developing roller 91 is so disposed as to make contact with the photoconductor drum 10. The feeding roller 92 is provided for feeding the liquid developer to the developing roller 91, and is brought into contact with a lower portion of the developing roller 91. The supporting roller 93 supports the liquid developer with the feeding roller 92, and is so disposed as to make contact with the feeding roller 92.

A doctor blade 921 is provided in such a way as to make contact with the feeding roller 92. The doctor blade 921 controls the liquid developer carried on the feeding roller 92 to be fed to the developing roller 91 to have a predetermined thickness. The developer feeding member 94 feeds the liquid developer onto a part of the supporting roller 93 in the immediate vicinity of a portion where the feeding roller 92 and the supporting roller 93 make contact with each other, the part being located upstream of that portion along a rotation direction of the supporting roller 93.

The developer remover 96 removes the liquid developer remaining on the developing roller 91 without being fed to the photoconductor drum 10. The developer remover 96 has a developer scraper blade 961 that is brought into contact with the developing roller 91 to scrape the liquid developer off the developing roller 91. The developer scraper blade 961 is located, along a rotation direction of the developing roller 91, downstream of the portion where the developing roller 91 and the photoconductor drum 10 make contact with each other. The developer charger 97 charges the toner contained in the liquid developer carried on the developing roller 91. The developer charger 97 is disposed near the developing roller 91.

The liquid developer fed onto the supporting roller 93 from the developer feeding member 94 is carried away by the feeding roller 92 that makes contact with the supporting roller 93, is then controlled by the doctor blade 921 so as to have a predetermined thickness, and is then adhered to the surface of the developing roller 91 that makes contact with the feeding roller 92. The liquid developer containing the toner particles that have not been fed to the developing roller 91 remains on the surface of the feeding roller 92. This residual liquid developer falls to the bottom of the developing device 9 by gravity, and is then collected by the second recovery container 83 (see FIG. 3) via the pipe 98.

The electric field (having the same polarity as the toner) created by the developer charger 97 facing the developing roller 91 makes the toner in the developer layer carried on the developing roller 91 move toward the surface of the developing roller 91. This helps offer greater developing efficiency than when the toner is randomly dispersed in the developer. The positively charged toner particles suspended in the liquid developer on the surface of the developing roller 91 move toward the photoconductor drum 10 because of an electric potential difference between the developing roller 91 to which the developing bias is applied and the photoconductor drum 10, and are then attached to a portion (an exposure portion) of the surface of the photoconductor drum 10, the portion being subjected to optical attenuation by the LED exposing device 12. In this way, the developing roller 91 develops the electrostatic latent image formed on the surface of the photoconductor drum 10 into a toner image by using the liquid developer fed from the feeding roller 92.

After completion of development, the liquid developer containing the toner particles that have not been used for development remains on the surface of the developing roller 91. This residual liquid developer is removed by the developer scraper blade 961 of the developer remover 96, and is then collected by the second recovery container 83 (see FIG. 3) via the pipe 99.

Figure 3:
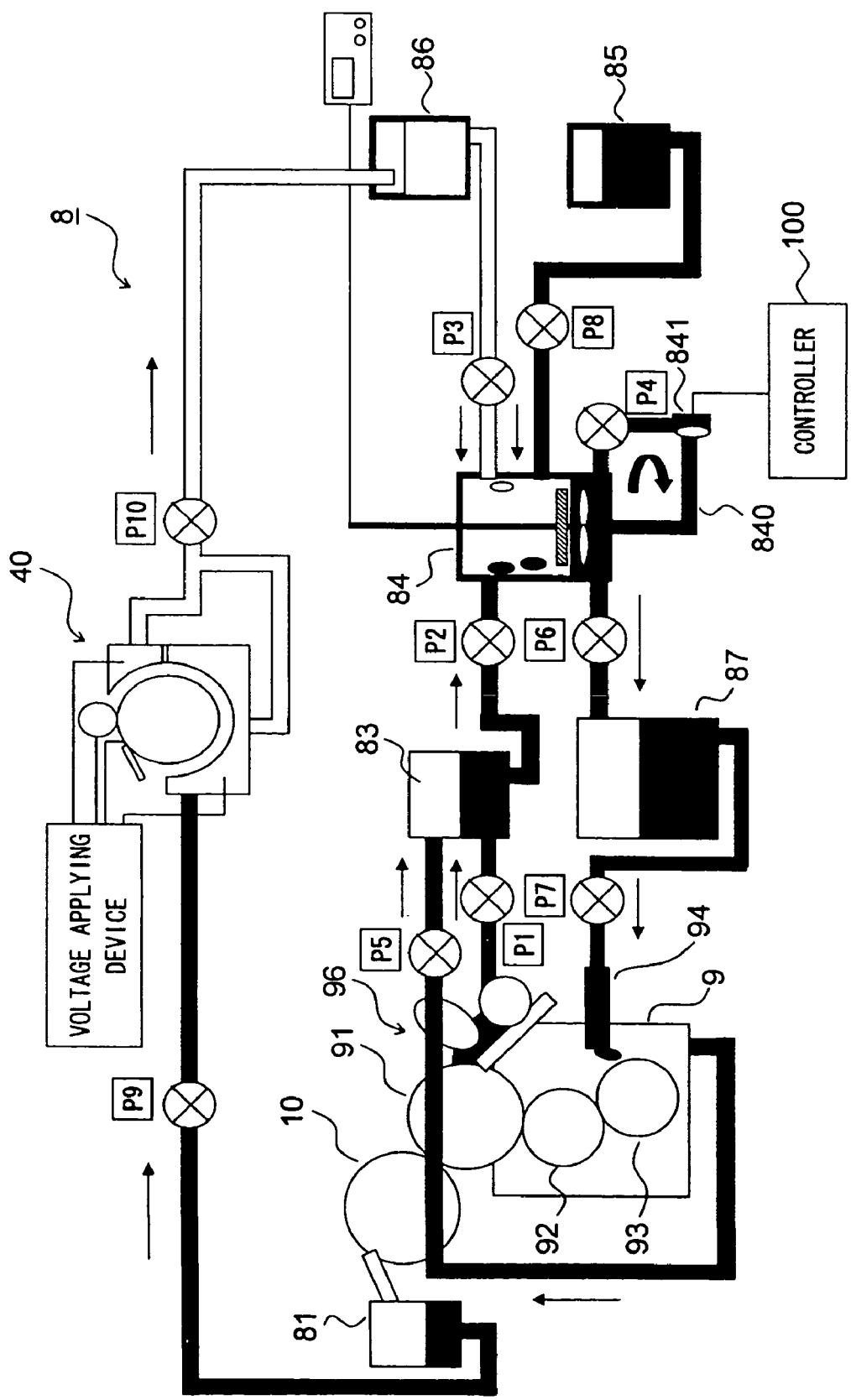
FIG. 3 shows an essential portion of the liquid developer circulating device provided in the image forming apparatus.

FIG. 3 shows an essential portion of the liquid developer circulating device 8. With reference to FIG. 3, the structure of the liquid developer circulating device 8 will be described. The liquid developer circulating devices 8 are provided one for each of the image forming portions 20C, 20M, 20Y, and 20B. The liquid developer circulating device 8 is provided for recycling the liquid developer that has not been used for image formation. As shown in FIG. 3, the liquid developer circulating device 8 is provided with a first recovery container 81, a separating device 40, a second recovery container 83, an adjustment container 84, a toner tank 85, a carrier tank 86, and a reservoir tank 87. The flow of the liquid developer through the liquid developer circulating device 8 is indicated by arrows in FIG. 3.

The first recovery container 81 collects the liquid developer conveyed by the residual developer conveying screw 261. The separating device 40 separates the liquid developer collected by the first recovery container 81 into toner and a carrier liquid, and is connected to the first recovery container 81 by a pipe through a pump P9. In this embodiment, only the carrier liquid separated by the separating device 40 is recycled, and the toner is discarded.

The second recovery container 83 stores the liquid developer removed from the developing roller 91 by the developer remover 96, and the surplus liquid developer that has fallen to the bottom of the developing device 9 without being fed to the developing roller 91 from the feeding roller 92. The second recovery container 83 is connected to the developing device 9 by a pipe provided with a pump P5, and to the developer remover 96 by a pipe provided with a pump P1.

The adjustment container 84 adjusts the toner concentration of the liquid developer within a specified range. The adjustment container 84 is connected to the second recovery container 83 by a pipe provided with a pump P2. To this adjustment container 84, a circulating pipe 840 is connected. The circulating pipe 840 is a ring-shaped pipe having two ends connected to different portions of the adjustment container 84. The circulating pipe 840 is provided with a pump P4 and a toner concentration sensor 841 serving as a toner concentration measuring device. With this structure, the liquid developer is made to circulate through the circulating pipe 840 from the adjustment container 84 and back into the adjustment container 84.

The toner concentration sensor 841 detects the toner concentration of the liquid developer circulating through the circulating pipe 840. The color printer 1 has a controller 100 provided with at least one CPU, at least one ROM, at least one RAM, and the like. Based on the detection results of the toner concentration sensor 841, the controller 100 can control the pumps P3, P6, and P8.

The toner tank 85 stores a liquid developer whose toner concentration is higher than that of the liquid developer used in the developing device 9, and is connected to the adjustment container 84 by a pipe provided with the pump P8. The carrier tank 86 stores a carrier liquid, and is connected to the adjustment container 84 by a pipe provided with the pump P3, and to the separating device 40 by a pipe provided with a pump P10. The reservoir tank 87 stores a liquid developer to be fed to the developing device 9, and is connected to the adjustment container 84 by a pipe provided with the pump P6, and to the developing device 9, more specifically, to the developer feeding member 94 by a pipe provided with a pump P7. The pumps send the liquid developer in one direction.

Next, with reference to FIG. 3, the circulation of the liquid developer will be described. The liquid developer remaining on the photoconductor drum 10 without being transferred to the intermediate transfer belt 21 from the photoconductor drum 10 at the time of image formation is removed from the photoconductor drum 10 by the drum cleaning blade 262, and is then collected by the first recovery container 81. The liquid developer collected by the first recovery container 81 is conveyed to the separating device 40 by the pump P9, and is then separated into toner and a carrier liquid. The carrier liquid thus separated is conveyed to the carrier tank 86 by the pump P10. In this embodiment, the toner separated from the carrier liquid is discarded.

The surplus liquid developer that has fallen to the bottom of the developing device 9 without being fed to the developing roller 91 from the feeding roller 92 is collected by the second recovery container 83 by the pump P5. On the other hand, the liquid developer removed from the developing roller 91 of the developing device 9 by the developer scraper blade 961 is collected by the second recovery container 83 by the pump P1. The liquid developer stored in the second recovery container 83 is conveyed to the adjustment container 84 by the pump P2. To the adjustment container 84, the toner and the carrier liquid are fed as required from the toner tank 85 and the carrier tank 86, respectively, such that the concentration of the liquid developer is adjusted. The liquid developer whose concentration is found to be within a specified range as a result of the adjustment is conveyed to the reservoir tank 87 by the pump P6. The liquid developer stored in the reservoir tank 87 is fed to the developer feeding member 94 by the pump P7.

The controller 100 obtains the toner concentration of the liquid developer stored in the adjustment container 84 based on the detection results of the toner concentration sensor 841, and adjusts the amount of toner to be fed from the toner tank 85 and the amount of carrier liquid to be fed from the carrier tank 86 by controlling the different pumps or the like, in such a way that the toner concentration falls within a specified range.

Next, the toner concentration measuring device according to the invention will be described with reference to the drawings. It is to be understood, however, that the toner concentration measuring device is not limited to the example specifically described below.

Figure 4A:
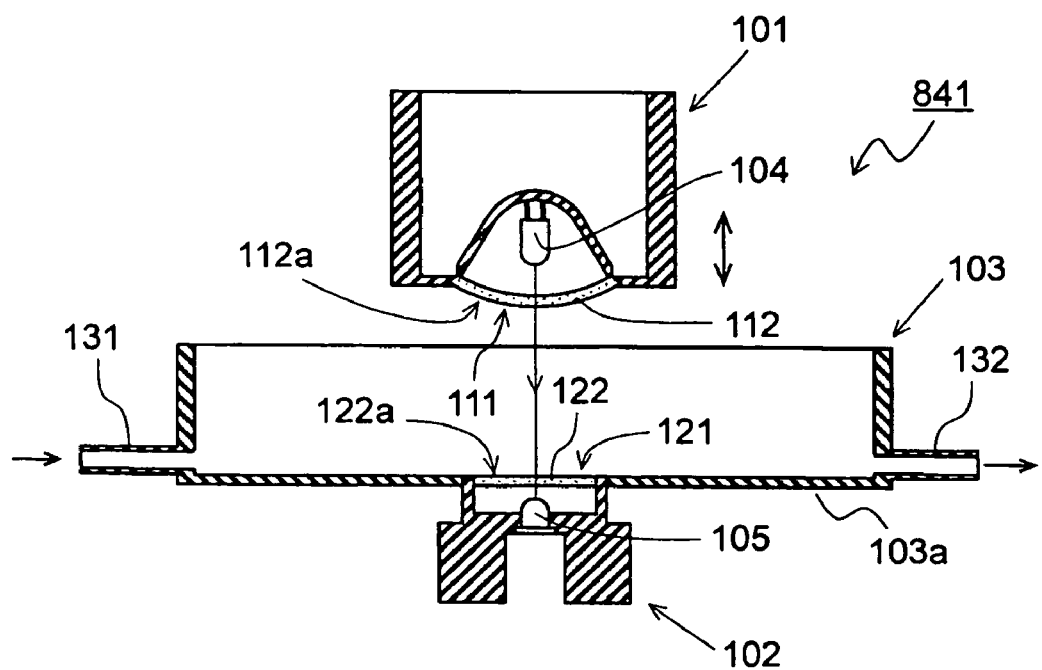
FIG. 4 are vertical sectional views showing an example of a toner concentration measuring device according to the invention.
Figure 4B:
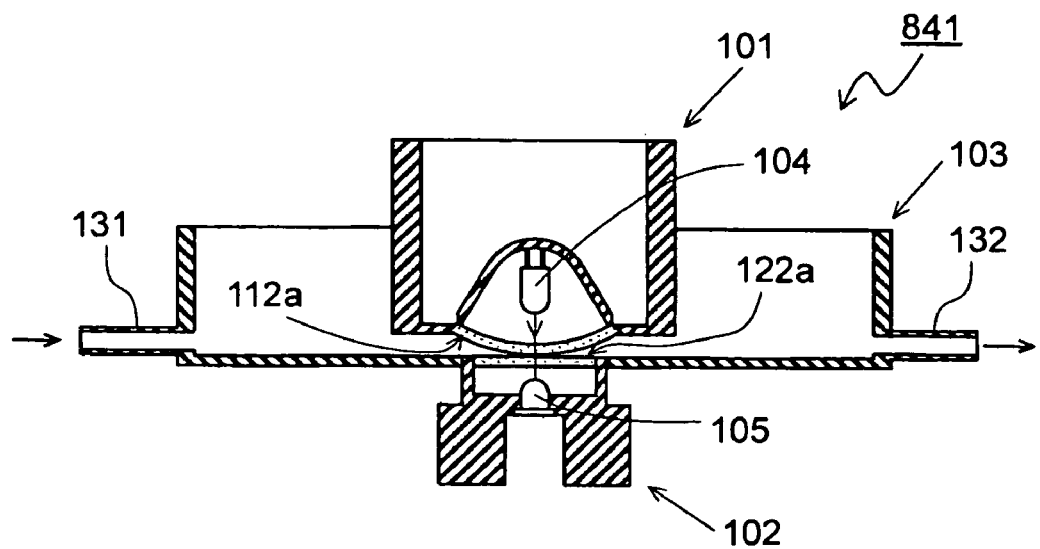

FIG. 4 are diagrams showing an outline of an example of a toner concentration measuring device according to the invention. Note that, in FIGS. 4A and 4B, such members as are found also in the conventional example shown in FIG. 12 will be identified with common reference characters. The toner concentration sensor 841 shown in FIGS. 4A and 4B serves as a toner concentration measuring device, and is provided with a measuring tank 103 through which the liquid developer (not shown) flows, a light-emitting portion 101 that can freely move up and down, and a light-receiving portion 102 that is fixed in position. The measuring tank 103 is a box-shaped member that is open in the upper face, and has an inlet 131 and an outlet 132 formed in the opposite side walls thereof so as to permit the liquid developer to flow into and out of the measuring tank 103. The liquid developer is made to flow through the measuring tank 103 by the pump P4 (see FIG. 3) at least when the toner concentration is measured.

The light-emitting portion 101 is provided with a light-emitting member 104 from which predetermined light is emitted, and a light exit 111 from which the light emitted from the light-emitting member 104 emerges. The light exit 111 is fitted with a first transparent member 112 in a watertight manner. The external surface of the first transparent member 112 serves as a light emergence surface 112a. The light emergence surface 112a of the first transparent member 112 is a spherical surface protruding downward (see FIG. 8A). It is to be noted that, in actuality, the external surface of the light emergence surface has a relatively large radius of curvature on the order of 400 mm. For the sake of simplification, however, in FIGS. 4A and 4B, the radius of curvature of the external surface of the light emergence surface is made smaller than it really is. The light-emitting member 104 is not limited to that specifically shown in the figure, but any conventionally known light-emitting member may be used instead. In a case where color toner is used, however, light of wavelengths in the infrared region is suitably used because different colors have different light absorption bands.

The light-receiving portion 102 is provided with a light entrance 121 through which light enters, and a light-receiving member 105 that receives the incident light. The light entrance 121 is fitted with a second transparent member 122 in a watertight manner. The external surface of the second transparent member 122 serves as a light incidence surface 122a. The light-receiving member 105 is not limited to that specifically shown in the figure, but any conventionally known light-receiving member may be used instead.

The light-receiving portion 102 is attached to a bottom wall 103a of the measuring tank 103 in such a way that the light incidence surface 122a of the second transparent member 122 fitted into the light entrance 121 is flush with the bottom of the measuring tank 103. On the other hand, the light-emitting portion 101 is disposed in such a way that the light emergence surface 112a faces the light incidence surface 122a. The light-emitting portion 101 is attached in such a way that it can be moved, by an unillustrated up-and-down mechanism, between a measurement position (FIG. 4B) where the light emergence surface 112a makes contact with the light incidence surface 122a and a waiting position (FIG. 4A) where the light emergence surface 112a is away from the light incidence surface 122a.

In the toner concentration sensor 841 structured as described above, when toner concentration is not measured, the light-emitting portion 101 is in a waiting position where the light emergence surface 112a is away from the light incidence surface 122a (FIG. 4A). This enables the liquid developer (not shown) to smoothly flow between the light emergence surface 112a and the light incidence surface 122a, preventing local accumulation of toner observed in the conventional example. Even if the toner particles are caught in the space between the light emergence surface 112a and the light incidence surface 122a when toner concentration is measured, they are flushed away by the liquid developer flowing between the light emergence surface 112a and the light incidence surface 122a when the light emergence surface 112a is moved away from the light incidence surface 122a.

Preferably, the light-emitting portion 101 is moved upward in the following manner. When the shortest distance between the light emergence surface 112a and the light incidence surface 122a becomes about half the thickness of the liquid developer flowing through the measuring tank 103, the upward movement of the light-emitting portion 101 is temporarily stopped. The light-emitting portion 101 is left in this position for a specified time. Then, the light-emitting portion 101 is moved upward again to the waiting position. Doing so makes the thickness of the liquid developer flowing between the light emergence surface 112a and the light incidence surface 122a temporarily thinner than that of the liquid developer flowing over the rest of the measuring tank 103 (a portion thereof that is not located directly below the light-emitting portion 101). As a result, the liquid developer flows between the light emergence surface 112a and the light incidence surface 122a at higher velocity than the liquid developer flowing over the rest of the measuring tank 103, making it possible to efficiently flush away the toner stuck to the light emergence surface 112a or the light incidence surface 122a as a result of being caught in the space between them.

When toner concentration is measured, the light-emitting portion 101 is moved downward from the waiting position to the measurement position by driving the unillustrated up-and-down mechanism, such that the light emergence surface 112a of the light-emitting portion 101 is brought into contact with the light incidence surface 122a of the light-receiving portion 102 (FIG. 4B). Since the light emergence surface 112a of the light-emitting portion 101 is a spherical surface protruding downward, the light emergence surface 112a makes contact with the light incidence surface 122a at a point. This eliminates the need to precisely control the spacing between the light emergence surface 112a and the light incidence surface 122a, making it possible to measure the toner concentration by measuring the amount of light passing through the liquid developer around the contact point with the light-receiving member 105.

Figure 5A:
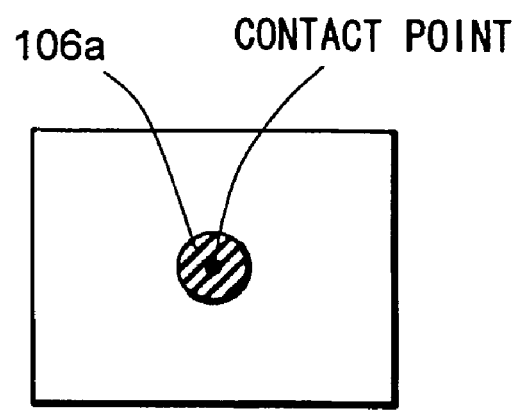
FIG. 5 are plan views each showing an example of a lightproof member.
Figure 5B:
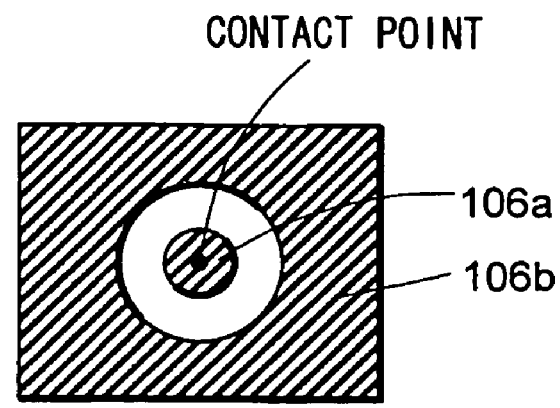

In the measuring device shown in FIGS. 4A and 4B, the direction in which the light-emitting member 104 emits light and the direction in which the light enters the light-receiving member 105 are on approximately the same axis. This helps increase the amount of light entering the light-receiving member 105, thereby enhancing the measurement accuracy. Incidentally, in the measuring device shown in FIGS. 4A and 4B, the optical axis is made to pass through the contact point between the light emergence surface 112a and the light incidence surface 122a. Inconveniently, however, doing so may increase the amount of light entering the light incidence surface 122a directly from the light emergence surface 112a without passing through the liquid developer, making smaller the ratio of a change in output of the light-receiving member 105 to a change in toner concentration. Therefore, as shown in FIG. 5A, it is preferable that a lightproof member 106a (FIG. 5A) be attached to a predetermined region around the contact point between the light emergence surface 112a and the light incidence surface 122a, thereby allowing the light-receiving member 105 to detect the light passing through the liquid developer. More preferably, a lightproof member 106b is additionally attached in such a way that a ring-shaped opening that is concentric with the lightproof member 106a is formed around the contact point (FIG. 5B), thereby preventing the light from portions other than the light-emitting portion 101 from entering the light-receiving member 105.

Figure 6:
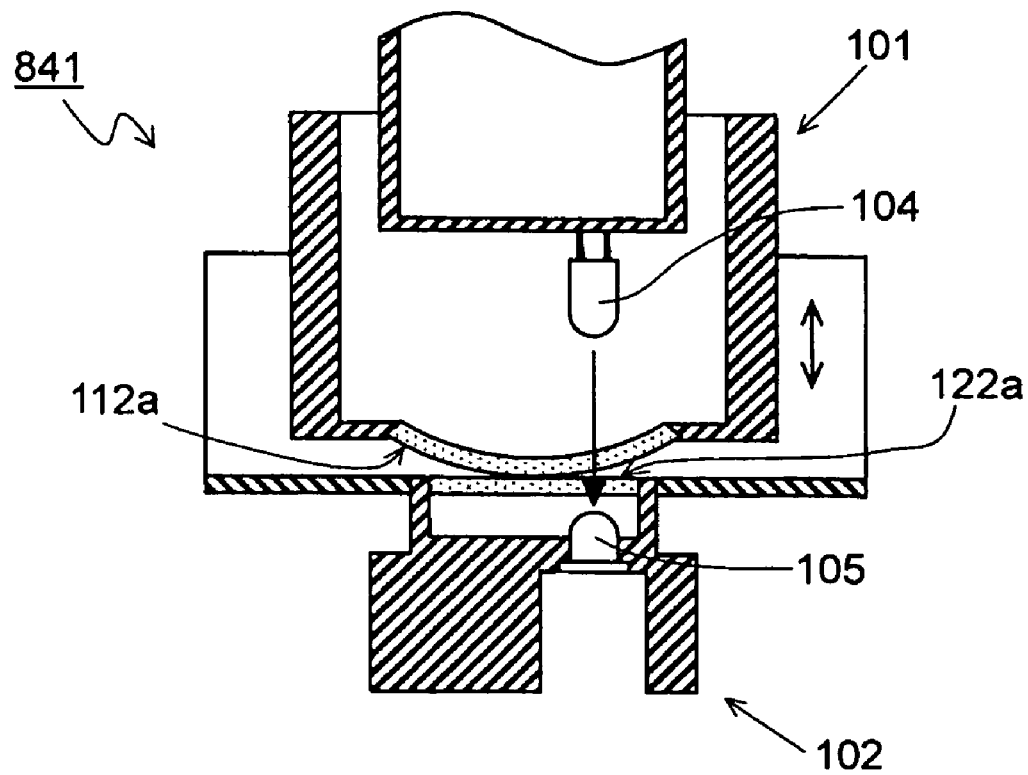
FIG. 6 is a vertical sectional view showing another example of the toner concentration measuring device according to the invention.

Alternatively, as shown in FIG. 6, the direction in which the light-emitting member 104 emits light and the direction in which the light enters the light-receiving member 105 may be on approximately the same axis, and the optical axis may be made to pass through a point other than the contact point between the light emergence surface 112a and the light incidence surface 122a. With this structure, since high-intensity light on the optical axis always passes through the liquid developer, the ratio of a change in output of the light-receiving member 105 to a change in toner concentration becomes large. This helps enhance the accuracy of the measurement of toner concentration.

Figure 7:
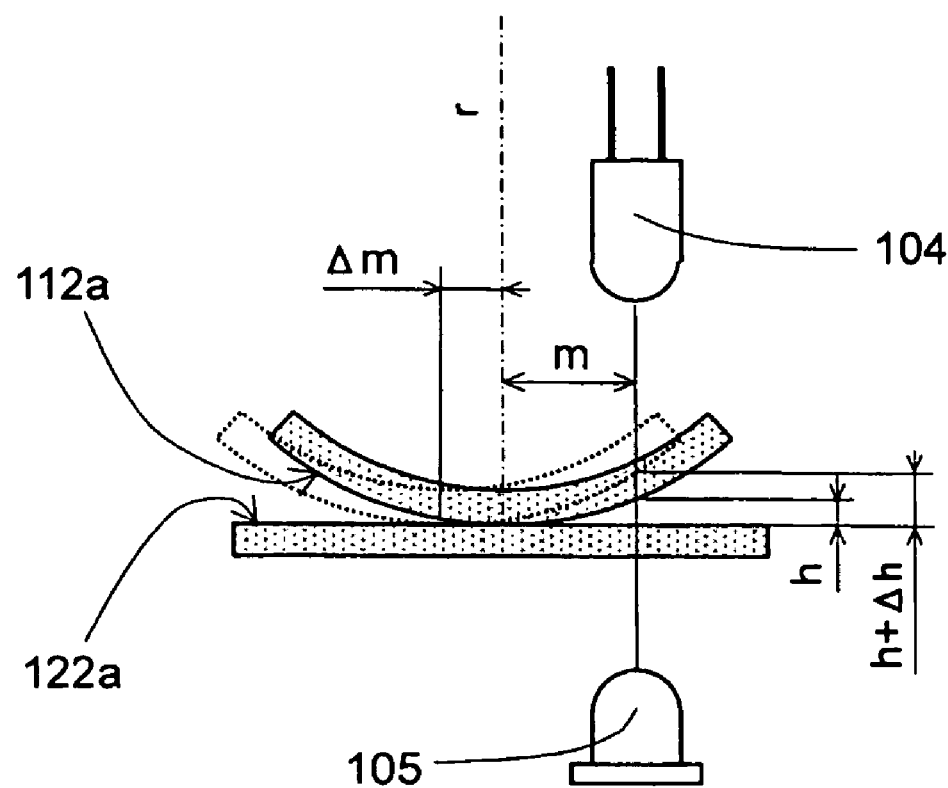
FIG. 7 is a vertical sectional view showing another example of the toner concentration measuring device according to the invention.

Alternatively, the light-emitting member 104 may be kept at a fixed distance from the light-receiving member 105 regardless of whether the light-emitting portion 101 is in the waiting position or in the measurement position, that is, the light-emitting member 104 may be fixed in a position so as not to be moved up and down along with the light emergence surface 112a, and the light emergence surface 112a may be given a radius of curvature of equal to or more than several tens of centimeters. Doing so ensures that the optical axis passes through a liquid developer having substantially uniform thickness even if the light emergence surface 112a is tilted or moved rightward or leftward due to an up-and-down motion, making it possible to perform stable measurement of toner concentration. FIG. 7 shows an outline of this structure. Preferably, an up-and-down mechanism of the light-emitting portion 101 is structured as follows. The light-emitting portion 101 is shaped like a cylinder, and a cylindrical supporting member is provided in such a way as to circumscribe the light-emitting portion 101, such that the light-emitting portion 101 can slidably move within the cylindrical supporting member. With this structure, it is possible to minimize the amount of tilting or rightward or leftward movement of the light emergence surface 112a due to an up-and-down motion.

In the measuring device shown in FIG. 7, the radius of curvature r of the light emergence surface 112a is set to 400 mm, such that the optical axis passes through a point at a distance of m (=5 mm) from the contact point. At this point, the thickness h of the liquid developer through which the optical axis passes is 0.0320 mm. Suppose that the contact point is moved $\Delta m$ (=0.06 mm) leftward from the above-described reference point ($\Delta m$ is the maximum amount of deviation with consideration given to tolerances or the like). Then, the thickness (h+$\Delta h$) of the liquid developer layer through which the optical axis passes is 0.0320 mm. In this case, the error $\Delta h$ is only 0.0008 mm (0.8 μm), which can be regarded as having an insignificant effect on the measurement.

Figure 8A:
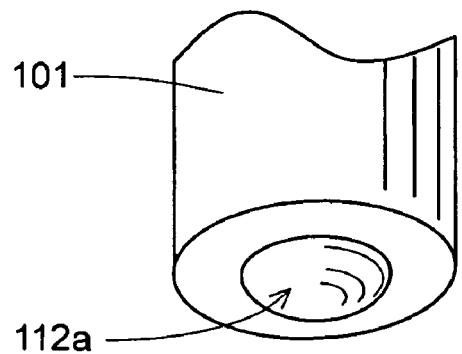
FIG. 8 are perspective views each showing an example of the outer shape of the light emergence surface.
Figure 8B:
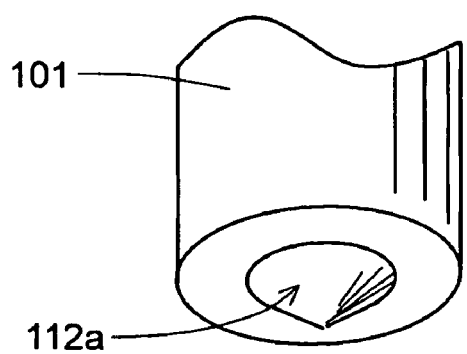
Figure 8C:
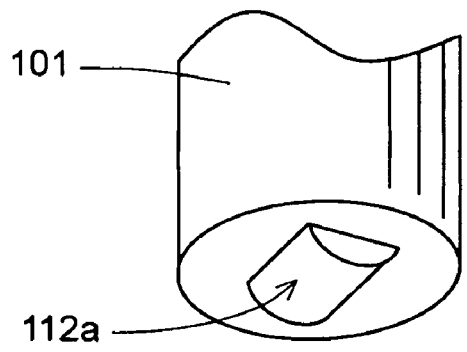
Figure 8D:
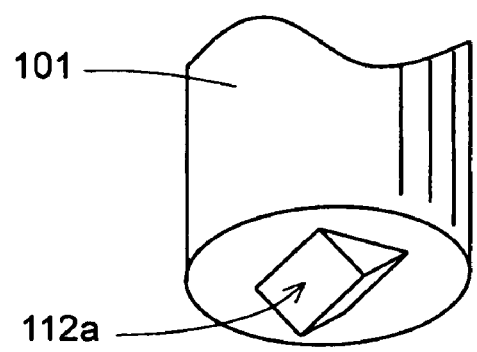

The light emergence surface 112a and the light incidence surface 122a according to the present invention simply have to have an outer shape that allows them to make contact with each other at a point or along a line. FIGS. 8A to 8D show typical examples of the outer shape. Note that FIGS. 8A to 8D are exaggerated for purposes of illustration. The light emergence surface 112a shown in FIG. 8A is spherical in shape and is adopted in the embodiment described above, and the light emergence surface 112a shown in FIG. 8B is conical in shape. If the light emergence surface 112a is spherical or conical in shape, the light emergence surface 112a makes contact with the light incidence surface 122a at a point. On the other hand, the light emergence surface 112a shown in FIG. 8C is a column-shaped member (part of a cylindrical column) whose cross section is semicircular, and the light emergence surface 112a shown in FIG. 8D is a triangular-prism-shaped member (part of a triangular prism). If the light emergence surface 112a is a column-shaped member or a triangular-prism-shaped member, the light emergence surface 112a makes contact with the light incidence surface 122a along a line. The descriptions heretofore deal solely with the examples of the outer shape of the light emergence surface 112a. Needless to say, however, the light incidence surface 122a may have any one of these outer shapes. From the viewpoint of achieving measurement with higher accuracy and stability, it is preferable that one of the light emergence surface 112a and the light incidence surface 122a have the above-described outer shape that allows them to make contact with each other at a point or along a line, and the other have a planar shape. More preferably, the light emergence surface 112a is spherical in shape, and the light incidence surface 122a is planar in shape.

Figure 9:
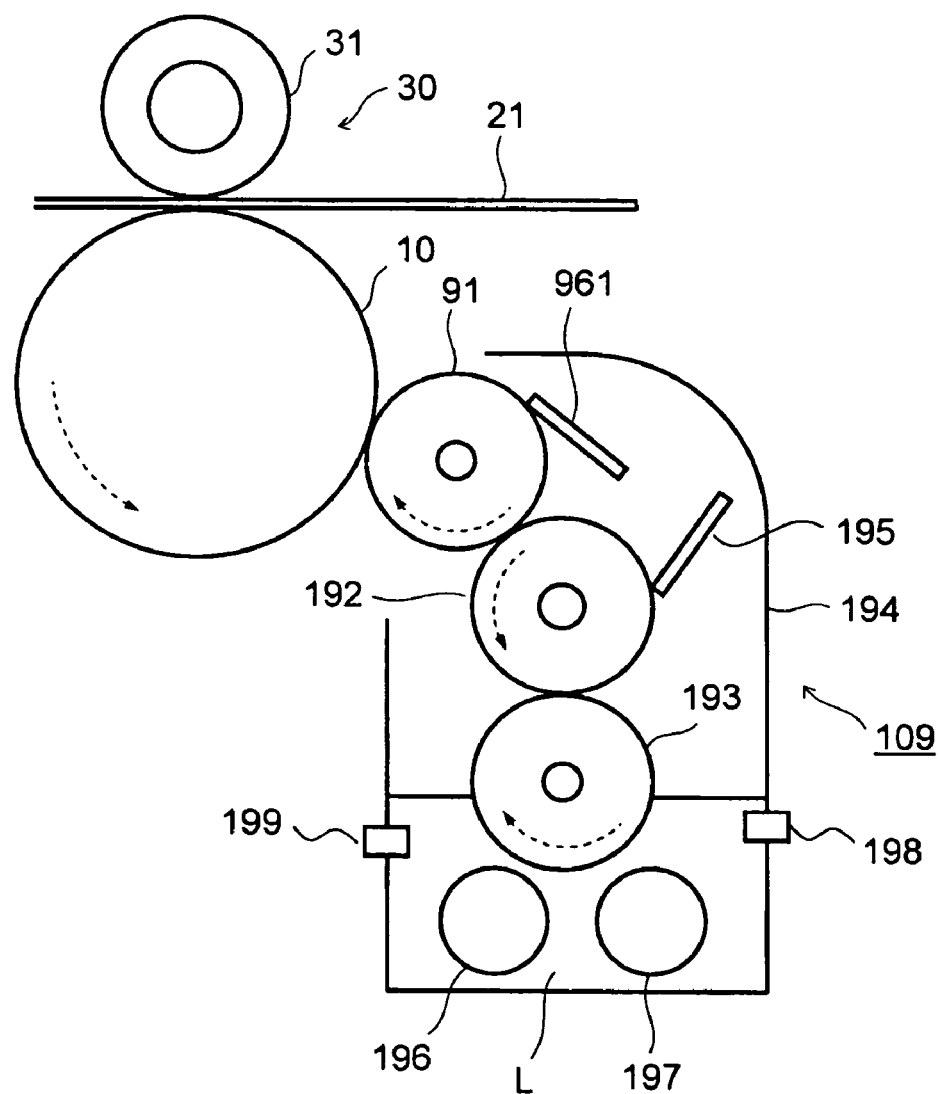
FIG. 9 is a vertical sectional view showing another example of the developing device incorporating the toner concentration measuring device according to the invention.

The embodiment described above deals with a case in which the toner concentration measuring device according to the present invention is used for measuring the concentration of toner in the liquid developer circulating device 8 that collects the liquid developer that has not been used for image formation, separates the collected liquid developer into toner and a carrier liquid, and then recycles the separated carrier liquid. However, it is also possible to use the toner concentration measuring device for detecting the concentration of the liquid developer in the rest of the image forming apparatus. For example, the toner concentration measuring device according to the present invention can be applied to a toner concentration sensor 199 and a part around it as a toner concentration measuring device of a developing device 109 shown in FIG. 9. The developing device 109 differs from the developing device 9 described above only in a mechanism for feeding a developer to the developing roller 91. In other respects, the developing device 109 has almost the same structure as the developing device 9. Therefore, such members as find their functionally equivalent counterparts in the embodiment described above are identified with the same reference characters, and the description thereof will be omitted.

The developing device 109 can be applied to the color printer 1 shown in FIG. 1 as a substitute for the developing device 9. Alternatively, the developing device 109 can be applied to another image forming apparatus, such as an image forming apparatus in which the liquid developer circulating device 8 shown in FIG. 3 is not provided, and toner and a carrier liquid are directly fed to the developing device 109 from the toner tank 85 and the carrier tank 86, respectively. In the following description, explanations will be given of a case where the developing device 109 is applied to the latter image forming apparatus, namely, the image forming apparatus in which toner and a carrier liquid are directly fed to the developing device 109.

The developing device 109 has a liquid developer container 194 that stores a liquid developer. As is the case with the developing device 9, inside the liquid developer container 194 are provided the developing roller 91 and the developer scraper blade 961. The developing device 109 includes, inside the liquid developer container 194, a feeding roller 192 and a pumping roller 193 in place of the feeding roller 92 and the supporting roller 93, respectively, of the developing device 9. The developing device 109 further includes a doctor blade 195 and spiral agitators 196 and 197. Furthermore, the developing device 109 is provided with a developer liquid level sensor 198 and a toner concentration sensor 199.

The spiral agitators 196 and 197 are provided in such a way as to be fully immersed in a liquid developer L stored in the liquid developer container 194 for agitation of the liquid developer L. The rotation of the spiral agitators 196 and 197 produces a uniform distribution of the toner particles in the carrier liquid. The feeding roller 192 and the pumping roller 193 are cylindrical rollers each having a rotation axis that is parallel to the rotation axis of the photoconductor drum 10. The feeding roller 192 and the pumping roller 193 can rotate about the rotation axes in the directions indicated by arrows shown in FIG. 9. The pumping roller 193 is so disposed as to be partially immersed in the liquid developer L stored in the liquid developer container 194. As the pumping roller 193 rotates, the liquid developer L is attached to the surface of the pumping roller 193 and is then pumped up.

The feeding roller 192 is so disposed as to make contact with the pumping roller 193, and is supplied with the liquid developer from the pumping roller 193. That is, the feeding roller 192 is disposed downstream of the flow of the liquid developer L along a rotation direction of the pumping roller 193 (a direction in which the liquid developer moves). The doctor blade 195 is located downstream of a position where the feeding roller 192 makes contact with the pumping roller 193 along a rotation direction of the feeding roller 192, and is located upstream of a position where the developing roller 91 and the feeding roller 192 makes contact with each other, which will be described later. The doctor blade 195 is located at a given distance from the feeding roller 192, so as to control the liquid developer on the surface of the feeding roller 192 to have a predetermined thickness.

The developing roller 91 is so disposed as to make contact with the feeding roller 192, such that the liquid developer is fed to the surface thereof from the feeding roller 192. The liquid developer remaining on the surface of the developing roller 91 that has completed the development on the photoconductor drum 10 is removed by the developer scraper blade 961 in the same manner as described above. The developer liquid level sensor 198 is disposed in the liquid developer container 194, so as to detect whether the liquid developer L stored in the liquid developer container 194 is at a predetermined level. If the liquid developer L is found to be at a lower level than a predetermined level, a concentrated liquid developer and a carrier liquid are fed in a given proportion to the liquid developer container 194 from the toner tank 85 and the carrier tank 86 (see FIG. 3), respectively. In this way, the liquid developer L is controlled so as to be at a predetermined level.

The toner concentration sensor 199 is a sensor for detecting the toner concentration of the liquid developer L stored in the liquid developer container 194. If the toner concentration detected by the toner concentration sensor 199 is found to be lower than a predetermined value, a concentrated liquid developer is fed to the liquid developer container 194 from the toner tank 85. In this way, the toner concentration is adjusted to be within a specified range. On the other hand, if the toner concentration detected by the toner concentration sensor 199 is found to be higher than a predetermined value, a carrier liquid is fed to the liquid developer container 194 from the carrier tank 86. In this way, the toner concentration is adjusted to be within a specified range. If the developer liquid level sensor 198 detects that the liquid level of the liquid developer L stored in the liquid developer container 194 becomes higher than a predetermined level during the adjustment of the toner concentration, an unillustrated drain pump provided at the bottom of the liquid developer container 194 is operated to drain the surplus developer into an unillustrated developer adjustment tank.

The invention may be practiced in any other manner than specifically described above, with any modification or variation made within the spirit of the invention. For example, the embodiment described above deals with a color printer adopting an intermediate transfer method as an image forming apparatus incorporating a toner concentration measuring device. However, needless to say, the present invention is applicable also to any other image forming apparatuses provided with wet developing devices, such as color copiers, black and white copiers, black and white printers, and facsimiles.

EXAMPLE

Figure 10:
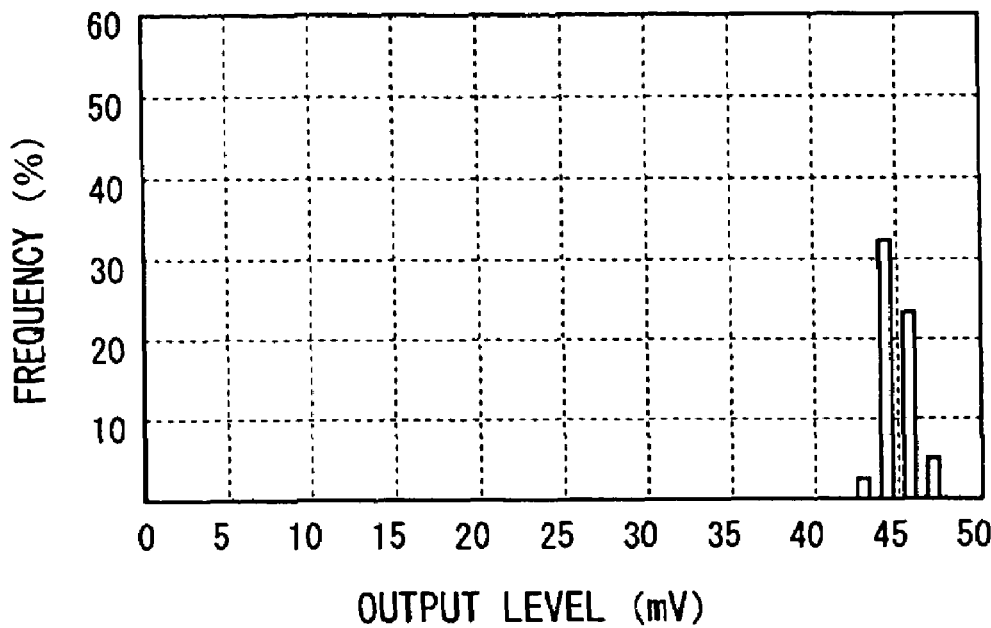
FIG. 10 is a graph showing the distribution of the frequency of an output level of a light-receiving element when the toner concentration measuring device shown in FIGS. 4A and 4B is used.

By using the toner concentration measuring device shown in FIGS. 4A and 4B, the toner concentration of a black liquid developer (with average toner particle size of 1.8 μm and toner concentration of 27%) was measured. Measurement was made by using a light-emitting member (LED) operating with a center wavelength of 940 nm with an output power of 20 mW, and by using as a light-receiving member a photodiode (PD410PI) manufactured by Sharp Corporation. FIG. 10 shows the distribution of the frequency of an output level of a light-receiving member, with the horizontal axis representing the output level and the vertical axis representing the frequency of an output level. As will be understood from FIG. 10, the output levels of the light-receiving element were concentrated in the range from 430 to 470 mV, indicating that the toner concentration was measured with high accuracy and stability.

COMPARATIVE EXAMPLE

Figure 11:
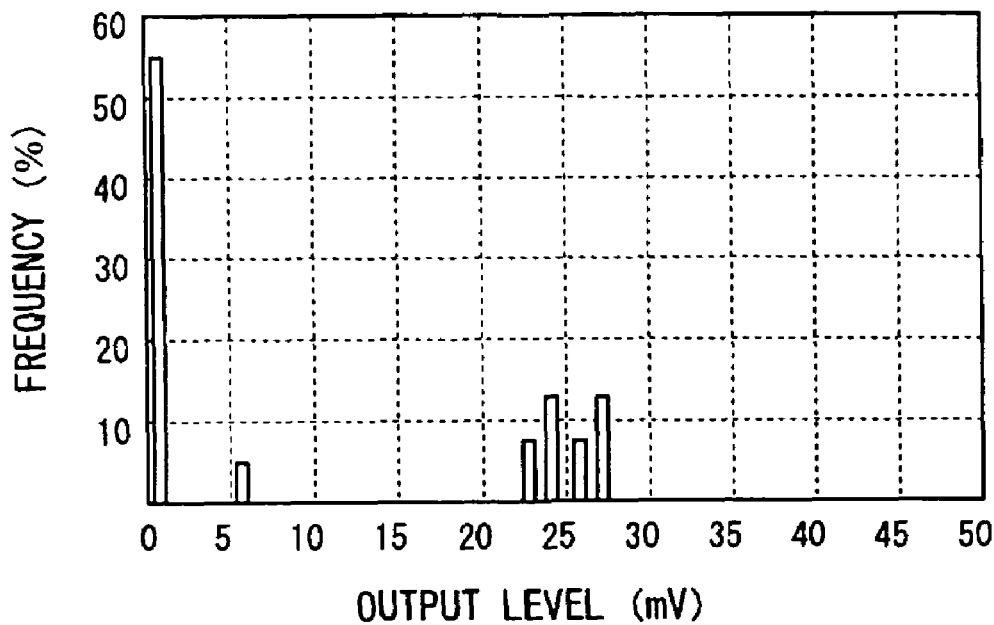
FIG. 11 is a graph showing the distribution of the frequency of an output level of a light-receiving element when a measuring device shown in FIG. 12 is used.
Figure 12A:
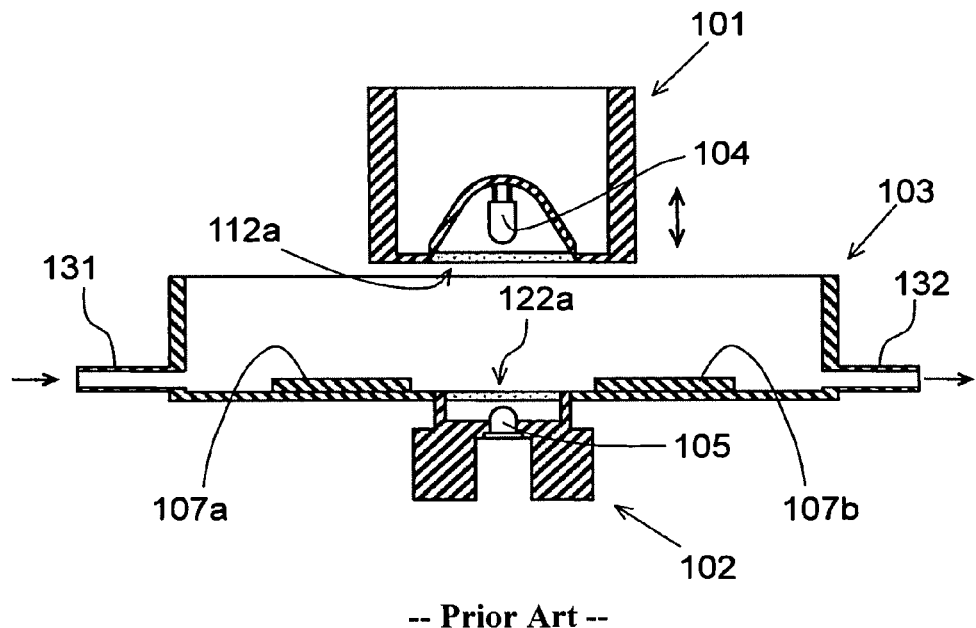
FIG. 12 are vertical sectional views showing a conventional toner concentration measuring device.
Figure 12B:
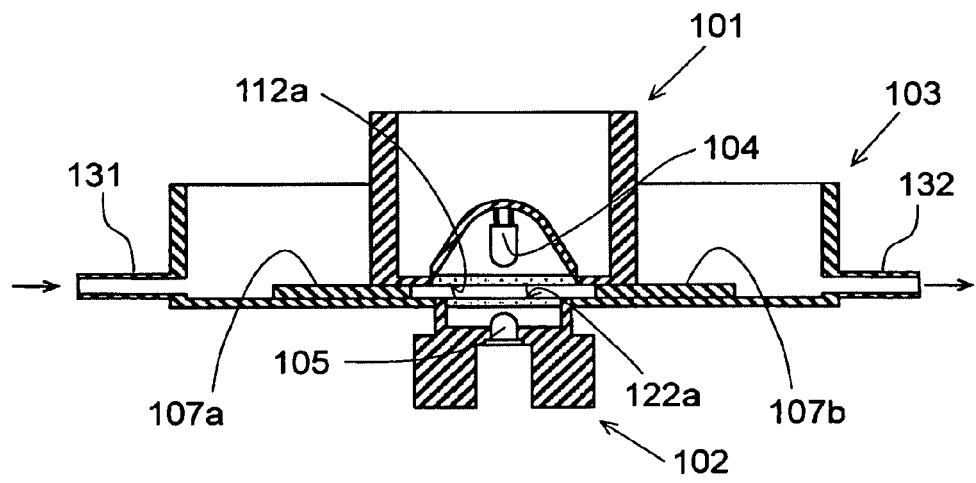
Figure 13:
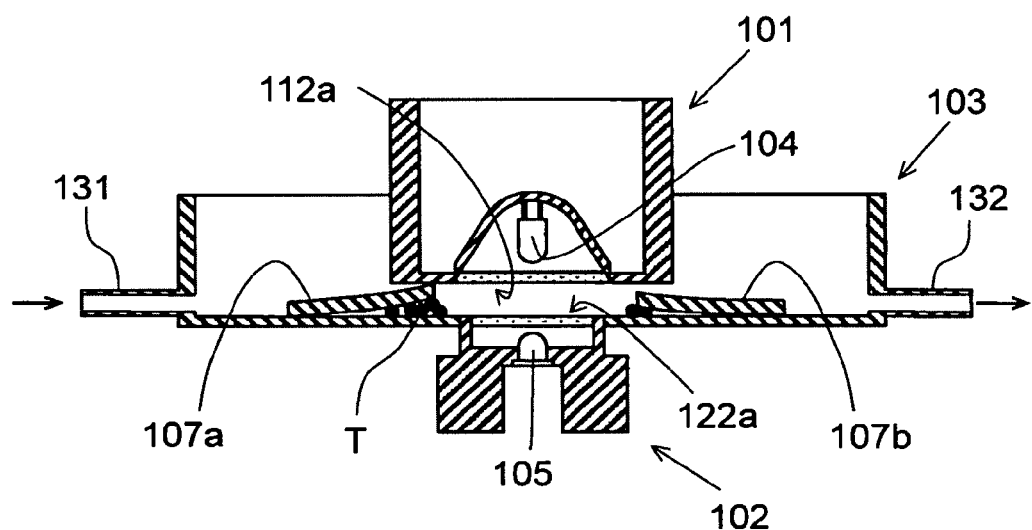
FIG. 13 is a vertical sectional view showing an example of a problem of the toner concentration measuring device shown in FIG. 12.

On the other hand, the toner concentration of a black liquid developer (with toner concentration of 27%) was measured in the same manner as described above by using a conventional toner concentration measuring device shown in FIGS. 12 and 13. The measurement was made under the same condition as the Example. FIG. 11 shows the distribution of the frequency of an output level of a light-receiving member, with the horizontal axis representing the output level and the vertical axis representing the frequency of an output level. As will be understood from FIG. 11, the output levels of the light-receiving element were distributed over a wide range including, 0 mV, 50 mV, and 230 to 270 mV, indicating that the toner concentration was measured with low accuracy and low stability.

What is claimed is:

1. A toner concentration measuring device for a liquid developer, comprising:
a light-emitting portion having a light-emitting member and a light emergence surface from which light from the light-emitting member emerges; and
a light-receiving portion having a light incidence surface through which the light from the light-emitting member enters and a light-receiving member that detects the light entering through the light incidence surface,
wherein the light emergence surface and the light incidence surface can make relative movement between a measurement position in which the light emergence surface and the light incidence surface make contact with each other and a waiting position in which the light emergence surface and the light incidence surface are away from each other,
the light emergence surface and the light incidence surface make contact with each other at a contact point or along a contact line in the measurement position.

2. The toner concentration measuring device of claim 1, wherein
at least one of the light emergence surface and the light incidence surface has a protruding portion protruding outward from the surface.

3. The toner concentration measuring device of claim 2, wherein
one of the light emergence surface and the light incidence surface is spherical in shape, and the other is planar in shape.

4. The toner concentration measuring device of claim 1, wherein
a direction in which the light-emitting member emits light and a direction in which the light enters the light-receiving member are on approximately a same axis,
the axis passes through a predetermined region including a point at which or a line along which the light emergence surface and the light incidence surface make contact with each other.

5. The toner concentration measuring device of claim 4, wherein
a lightproof member is attached to a predetermined region around the contact point or the contact line, the predetermined region of at least one of the light emergence surface and the light incidence surface.

6. The toner concentration measuring device of claim 5, wherein
the lightproof member is formed with a first lightproof member covering the contact point or the contact line and a second lightproof member that is attached around the first lightproof member leaving a space between the first lightproof member and the second lightproof member.

7. The toner concentration measuring device of claim 1, wherein
a direction in which the light-emitting member emits light and a direction in which the light enters the light-receiving member are on approximately a same axis,
the axis passes outside of a predetermined region including a point at which or a line along which the light emergence surface and the light incidence surface make contact with each other.

8. The toner concentration measuring device of claim 1, wherein
the light-emitting member and the light-receiving member are at a fixed distance from each other regardless of whether in the waiting position or in the measurement position.

9. An image forming apparatus comprising:
a wet developing device developing a latent image formed on an image supporting member by using a liquid developer made of a carrier liquid and toner particles suspended in the carrier liquid; and
a toner concentration measuring device comprising:
a light-emitting portion having a light-emitting member and a light emergence surface from which light from the light-emitting member emerges; and
a light-receiving portion having a light incidence surface through which the light from the light-emitting member enters and a light-receiving member that detects the light entering through the light incidence surface,
wherein the light emergence surface and the light incidence surface can make relative movement between a measurement position in which the light emergence surface and the light incidence surface make contact with each other and a waiting position in which the light emergence surface and the light incidence surface are away from each other,
the light emergence surface and the light incidence surface make contact with each other at a contact point or along a contact line in the measurement position.

10. The image forming apparatus of claim 9, wherein
at least one of the light emergence surface and the light incidence surface has a protruding portion protruding outward from the surface.

11. The image forming apparatus of claim 10, wherein
one of the light emergence surface and the light incidence surface is spherical in shape, and the other is planar in shape.

12. The image forming apparatus of claim 9, wherein
a direction in which the light-emitting member emits light and a direction in which the light enters the light-receiving member are on approximately a same axis,
the axis passes through a predetermined region including a point at which or a line along which the light emergence surface and the light incidence surface make contact with each other.

13. The image forming apparatus of claim 12, wherein
a lightproof member is attached to a predetermined region around the contact point or the contact line, the predetermined region of at least one of the light emergence surface and the light incidence surface.

14. The image forming apparatus of claim 13, wherein
the lightproof member is formed with a first lightproof member covering the contact point or the contact line and a second lightproof member that is attached around the first lightproof member leaving a space between the first lightproof member and the second lightproof member.

15. The image forming apparatus of claim 9, wherein
a direction in which the light-emitting member emits light and a direction in which the light enters the light-receiving member are on approximately a same axis,
the axis passes outside of a predetermined region including a point at which or a line along which the light emergence surface and the light incidence surface make contact with each other.

16. The image forming apparatus of claim 9, wherein the light-emitting member and the light-receiving member are at a fixed distance from each other regardless of whether in the waiting position or in the measurement position.

17. A toner concentration measuring method for a liquid developer,
the toner concentration measuring method using a toner concentration measuring device comprising:
a light-emitting portion having a light-emitting member and a light emergence surface from which light from the light-emitting member emerges; and
a light-receiving portion having a light incidence surface through which the light from the light-emitting member enters and a light-receiving member that detects the light entering through the light incidence surface,
the toner concentration measuring method comprising the steps of;
making the light emergence surface and the light incidence surface make relative movement in a measuring tank toward a measurement position in which the light emergence surface and the light incidence surface make contact with each other at a contact point or along a contact line;
receiving the light emitted from the light-emitting member by the light-receiving member; and
making the light emergence surface and the light incidence surface make relative movement in the measuring tank toward a waiting position in which the light emergence surface and the light incidence surface are away from each other.

18. The toner concentration measuring method of claim 17,
wherein the light emergence surface or the light incidence surface is moved from the measurement position to the waiting position in such a way that, when a shortest distance between the light emergence surface and the light incidence surface becomes about half a thickness of a liquid developer flowing through the measuring tank, a movement of the light-emitting portion or the light-receiving portion is temporarily stopped, the light-emitting portion or the light-receiving portion is left in this position for a specified time, and then the light emergence surface or the light incidence surface is finally moved to the waiting position.

* * * * *